(12) United States Patent
Zou et al.

(10) Patent No.: US 10,610,152 B2
(45) Date of Patent: Apr. 7, 2020

(54) SLEEP STATE DETECTION METHOD, APPARATUS AND SYSTEM

(71) Applicant: Xiaomi Inc., Beijing (CN)

(72) Inventors: Yixing Zou, Beijing (CN); Minghao Li, Beijing (CN); Guangjian Wang, Beijing (CN)

(73) Assignee: Xiaomi Inc., Beijing (CN)

( * ) Notice: Subject to any disclaimer, the term of this patent is extended or adjusted under 35 U.S.C. 154(b) by 676 days.

(21) Appl. No.: 15/360,344

(22) Filed: Nov. 23, 2016

(65) Prior Publication Data

US 2017/0143252 A1 May 25, 2017

(30) Foreign Application Priority Data

Nov. 24, 2015 (CN) .......................... 2015 1 0825157

(51) Int. Cl.
*A61B 5/00* (2006.01)
*A61B 5/11* (2006.01)
*H04M 1/725* (2006.01)

(52) U.S. Cl.
CPC ............ *A61B 5/4809* (2013.01); *A61B 5/002* (2013.01); *A61B 5/486* (2013.01); *A61B 5/6801* (2013.01);
(Continued)

(58) Field of Classification Search
CPC ........ A61B 2505/07; A61B 2560/0209; A61B 2560/0271; A61B 5/002; A61B 5/1118; A61B 5/4809; A61B 5/486; A61B 5/6801; A61B 5/6802; A61B 5/6898; A61B 5/721; A61B 5/7225
See application file for complete search history.

(56) References Cited

U.S. PATENT DOCUMENTS

2004/0225907 A1  11/2004  Jain et al.
2004/0230398 A1  11/2004  Okada et al.
(Continued)

FOREIGN PATENT DOCUMENTS

CN     1415085 A     4/2003
CN     1550210 A    12/2004
(Continued)

OTHER PUBLICATIONS

International Preliminary Report on Patentability and Written Opinion dated May 29, 2018 in PCT/CN2015/099614 (with English language translation), 11 pages.
(Continued)

*Primary Examiner* — Michael W Kahelin
*Assistant Examiner* — Vynn V Huh
(74) *Attorney, Agent, or Firm* — Oblon, McClelland, Maier & Neustadt, L.L.P.

(57) ABSTRACT

Aspects of the disclosure include a sleep state detection method. The sleep state detection method includes: upon detecting that current status of a user satisfies a preset sleep condition, sending, by a smart wearable device, a state checking request to a terminal associated with the smart wearable device, the state checking request instructing the terminal to provide state information based on sensor data or an operation event of a predetermined application on the terminal; receiving the state information from the terminal; and determining whether the user enters a sleep state based on the state information.

16 Claims, 13 Drawing Sheets

(52) U.S. Cl.
CPC .......... *A61B 5/6802* (2013.01); *A61B 5/6898* (2013.01); *A61B 5/721* (2013.01); *A61B 5/7225* (2013.01); *A61B 5/1118* (2013.01); *A61B 2505/07* (2013.01); *A61B 2560/0209* (2013.01); *A61B 2560/0271* (2013.01)

(56) References Cited

U.S. PATENT DOCUMENTS

| | | | |
|---|---|---|---|
| 2015/0094544 A1 | 4/2015 | Spolin et al. | |
| 2015/0148093 A1 | 5/2015 | Huang et al. | |
| 2015/0164430 A1 | 6/2015 | Hu et al. | |
| 2015/0181368 A1 | 6/2015 | Okabayashi | |
| 2015/0182139 A1 | 7/2015 | Kanishima et al. | |
| 2015/0182164 A1 | 7/2015 | Utter, II | |
| 2015/0289821 A1 | 10/2015 | Rack-Gomer et al. | |
| 2015/0289823 A1 | 10/2015 | Rack-Gomer et al. | |
| 2015/0296596 A1 | 10/2015 | Lee et al. | |
| 2016/0066018 A1* | 3/2016 | Chesluk | H04N 21/6587 725/25 |

FOREIGN PATENT DOCUMENTS

| | | | |
|---|---|---|---|
| CN | 104598130 A | | 5/2015 |
| CN | 105004019 A | | 10/2015 |
| CN | 105042769 A | * | 11/2015 |
| CN | 105042769 A | | 11/2015 |
| CN | 105045386 A | | 11/2015 |
| JP | 2015-107743 A | | 6/2015 |
| KR | 10-2015-0118827 A | | 10/2015 |
| RU | 79 769 U1 | | 1/2009 |
| RU | 2013 100 382 A | | 7/2014 |
| WO | 2011/158198 A2 | | 12/2011 |

OTHER PUBLICATIONS

Office Action dated Apr. 18, 2018 in Russian Patent Application No. 2016134773, 13 pages.
Extended European Search Report dated May 3, 2017 in Patent Application No. 16200559.9.
Office Action dated Jan. 30, 2018 in Japanese Patent Application No. 2016-524070.
Combined Office Action and Search Report dated Jan. 4, 2018 in Chinese Patent Application No. 201510825157.2 (with English translation of categories of cited documents) citing documents AA-AB and AP-AR therein, 19 pages.
International Search Report dated Aug. 2, 2016, issued in PCT Application No. PCT/CN2015/099614.
Korean Office Action dated Aug. 11, 2017 in Korean Patent Apptication No. 10-2016-7009819.
Combined Russian Office Action and Search Report dated Aug. 11, 2017 in Russian Patent Application No. 2016134773.
Emad Malaekah, et al., "Automatic Detection of the Wake and Stage 1 Sleep Stages using the EEG Sub-Epoch Approach", Conf. Proc. IEEE Eng. Med Biol. Soc., Jul. 2013, pp. 6401-6404.

* cited by examiner

SLEEP STATE DETECTION METHOD, APPARATUS AND SYSTEM

CROSS-REFERENCE TO RELATED APPLICATIONS

This application claims priority of the Chinese Patent Application No. 201510825157.2, filed on Nov. 24, 2015, which is incorporated herein by reference in its entirety.

TECHNICAL FIELD

The present disclosure is related to the technical field of data processing, and more particularly, to a sleep state detection method, a sleep state detection apparatus and a sleep state detection system.

BACKGROUND

Wearable devices are portable devices which are worn directly by users or integrated into users' clothes or accessories. Wearable devices are capable of performing powerful functions through software support, data interaction and cloud interaction. Wearable devices will significantly change our life and perception of the world. Currently, when it is worn by a user, a wearable device may determine the user's sleep duration by collecting the user's moving states.

SUMMARY

Aspects of the disclosure include a sleep state detection method. The sleep state detection method includes: upon detecting that current status of a user satisfies a preset sleep condition, sending, by a smart wearable device, a state checking request to a terminal associated with the smart wearable device, the state checking request instructing the terminal to provide state information based on sensor data or an operation event of a predetermined application on the terminal; receiving the state information from the terminal; and determining whether the user enters a sleep state based on the state information.

In an embodiment, the state information includes a current state of the predetermined application indicating whether the predetermined application is in an awake state or a non-awake state. In an embodiment, the determining whether the user enters the sleep state based on the state information includes: determining that the user does not enter the sleep state, when the current state of the predetermined application is the awake state; and determining that the user enters the sleep state, when the current state of the predetermined application is the non-awake state.

In an embodiment, the sleep state detection method further includes upon detecting that the current status of the user satisfies the preset sleep condition, determining whether a sleep state filtering function is enabled. The state checking request is sent to the terminal when it is determined that the sleep state filtering function is enabled.

In an embodiment, the sleep state detection method further includes, when it is determined that the user enters the sleep state, sending a notification to the terminal notifying that the user enters the sleep state.

Aspects of the disclosure include a sleep state detection method. The sleep state detection method includes: receiving a state checking request from a smart wearable device indicating that the smart wearable device detects that current status of a user satisfies a preset sleep condition; checking, by a terminal, sensor data or an operation event of a predetermined application on the terminal according to the state checking request; and sending state information to the smart wearable device based on the sensor data or the operation event of the predetermined application on the terminal, so that the smart wearable device determines whether the user enters a sleep state based on the state information.

In an embodiment, the state information includes a current state of the predetermined application indicating whether the predetermined application is in an awake state or a non-awake state. In an embodiment, checking the sensor data or the operation event of the predetermined application on the terminal includes: determining whether the predetermined application receives a touch operation within a preset time period; when it is determined that the predetermined application does not receive a touch operation within the preset time period, determining that the current state of the predetermined application is the non-awake state; and when it is determined that the predetermined application receives a touch operation within the preset time period, determining that the current state of the predetermined application is the awake state.

In an embodiment, the state information includes a current state of the predetermined application indicating whether the predetermined application is in an awake state or a non-awake state. In an embodiment, checking the sensor data or the operation event of the predetermined application on the terminal includes: outputting a prompt for closing the predetermined application; when a feedback command corresponding to the prompt is received within a preset time period, determining that the current state of the predetermined application is the awake state; and when no feedback command corresponding to the prompt is received within the preset time period, determining that the current state of the predetermined application is the non-awake state.

In an embodiment, the sleep state detection method further includes, prior to checking the sensor data or the operation event of the predetermined application on the terminal, determining whether a sleep state filtering function is enabled, upon receiving the state checking request. When it is determined that the sleep state filtering function is enabled, the sensor data or the operation event of the predetermined application on the terminal are checked.

In an embodiment, the sleep state detection method further includes: receiving a notification from the smart wearable device, the notification notifying that the user enters the sleep state; and closing the predetermined application according to the notification.

In an embodiment, the sleep state detection method further includes: receiving an application setting command; and setting the predetermined application according to the application setting command.

Aspects of the disclosure include a sleep state detection apparatus that includes a processor and a memory for storing instructions executable by the processor. The processor is configured to: upon detecting that current status of a user satisfies a preset sleep condition, send a state checking request to a terminal associated with a smart wearable device, the state checking request instructing the terminal to provide state information based on sensor data or an operation event of a predetermined application on the terminal; receive the state information from the terminal; and determine whether the user enters a sleep state based on the state information.

Aspects of the disclosure include a sleep state detection apparatus that includes a processor and a memory for storing instructions executable by the processor. The processor is configured to: receive a state checking request from a smart wearable device indicating that the smart wearable device detects that current status of a user satisfies a preset sleep condition; check sensor data or an operation event of a predetermined application on a terminal according to the state checking request; and send state information to the smart wearable device based on the sensor data or the operation event of the predetermined application on the terminal, so that the smart wearable device determines whether the user enters a sleep state based on the state information.

BRIEF DESCRIPTION OF THE DRAWINGS

The accompanying drawings, which are incorporated in and constitute a part of this specification, illustrate embodiments consistent with the disclosure and, together with the description, serve to explain the principles of the disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise presented. The embodiments set forth in the following description of exemplary embodiments do not represent all embodiments consistent with the disclosure. Instead, they are merely examples of apparatuses and methods consistent with aspects related to the disclosure as recited in the appended claims.

Figure 1:
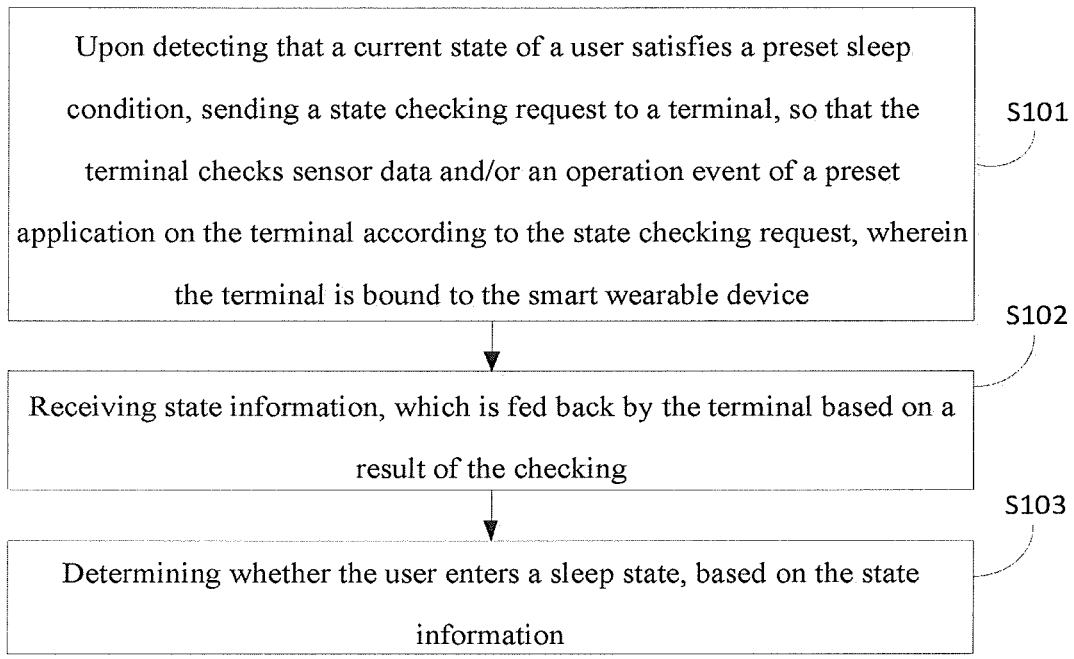
FIG. 1 is a flow chart showing a sleep state detection method according to an exemplary embodiment.

The disclosure provides a sleep state detection method, which is applicable to a smart wearable device. As shown in FIG. 1, the method comprises steps S101-S103.

In step S101, when it is detected that status information indicating current status of a user satisfies a preset sleep condition, a state checking request is sent to a terminal, so that the terminal checks, e.g., to query or access, sensor data and/or an operation event of a preset application on the terminal according to the state checking request, wherein the terminal is bound to the smart wearable device.

In step S102, state information, which is fed back by the terminal based on a result of the checking, is received.

In step S103, it is determined whether the user enters a sleep state, based on the state information.

In this embodiment, when detecting that the current status of the user satisfies the preset sleep condition (i.e., when detecting that the user may have entered the sleep state), the smart wearable device sends a state checking request to the terminal. The state checking request instructs the terminal to provide state information based on sensor data and/or an operation event of a predetermined application on the terminal. As such, the terminal checks the sensor data and/or the operation event of the predetermined application on the terminal and the smart wearable device determines whether the user enters the sleep state based on the state information fed back by the terminal. In this manner, the smart wearable device determines whether the user enters the sleep state with the assistance of the terminal, thereby preventing the smart wearable device from miscalculating the user's sleep duration and even misjudging that a sleep quality problem occurs, ensuring the accuracy of calculating the user's sleep duration and improving the user experience.

The terminal may send the sensor data and/or the operation event of the predetermined application it acquires to the smart wearable device as the state information. Of course, it is also possible that the terminal determines the state information thereof (such as a current state indicating whether the predetermined application is in an awake state or a non-awake state) based on the sensor data and/or the operation event of the predetermined application and then sends the determined state information to the smart wearable device.

Determining whether the user enters the sleep state based on the sensor data on the terminal comprises: judging whether the terminal remains stationary for a preset time period. If so, it may be deemed that the user is asleep and it is thus determined that the user enters the sleep state. Otherwise, if the terminal is in a non-stationary state for the preset time period, it indicates that the terminal is still used by the user and it is thus determined that the user does not enter the sleep state.

Figure 2:
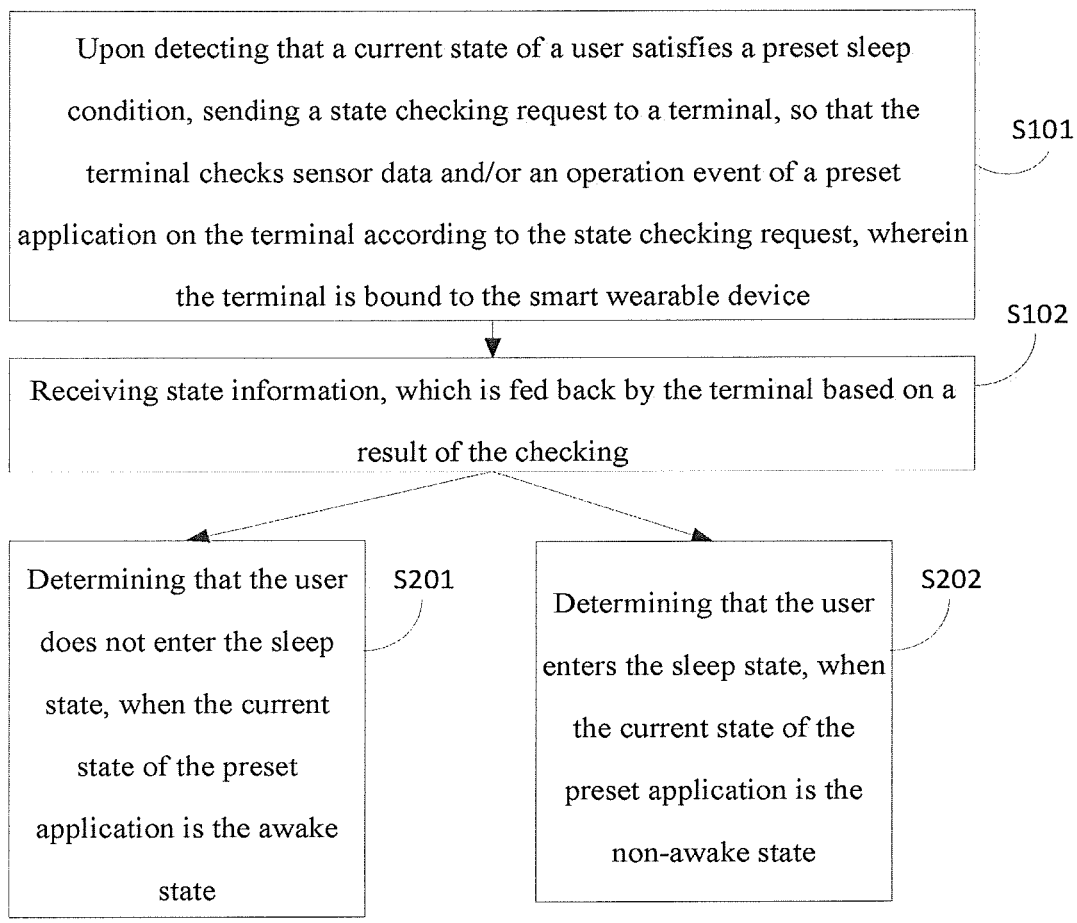
FIG. 2 is a flow chart showing a sleep state detection method according to another exemplary embodiment.

As shown in FIG. 2, in an embodiment, a current state of the predetermined application comprises an awake state or a non-awake state and the above-describe step S103 comprises steps S201-S202.

In step S201, it is determined that the user does not enter the sleep state, when the current state of the predetermined application is the awake state.

In step S202, it is determined that the user enters the sleep state, when the current state of the predetermined application is the non-awake state.

In this embodiment, if it is detected that the user performs an operation with respect to the predetermined application, it is deemed that the predetermined application is in the awake state; otherwise, it is deemed that the preset application is in the non-awake state. In this manner, it is determined whether the user is in the sleep state based on whether the user operates the predetermined application (i.e., whether the predetermined application is in an awake state or in a sleep state). This can ensure the accuracy of the judgment, thereby improving the user experience.

Figure 3:
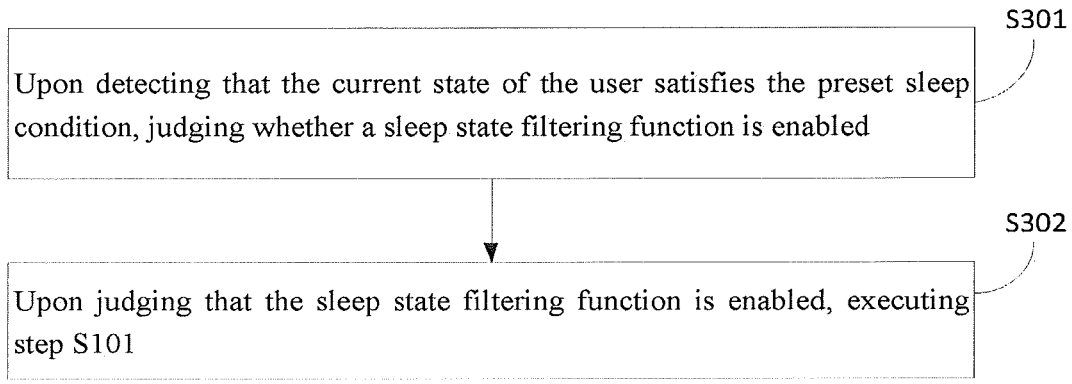
FIG. 3 is a flow chart showing a sleep state detection method according to yet another exemplary embodiment.

As shown in FIG. 3, in an embodiment, the method further comprises steps S301-S302.

In step S301, when it is detected that the current status of the user satisfies the preset sleep condition, it is determined whether a sleep state filtering function is enabled.

In step S302, when it is determined that the sleep state filtering function is enabled, the above-described step S101 is executed.

In this embodiment, the user may enable the sleep state filtering function according to personal needs. If the function is enabled, then the state checking request is sent to the terminal when the smart wearable device detects that the current status of the user satisfies the preset sleep condition. Accordingly, the sleep state of the user is determined based on the state information fed back by the terminal, so as to ensure the accuracy of the determination result. If the function is not enabled, then it is directly determined that the user enters the sleep state. In this manner, different needs of different users can be satisfied, thereby further improving the user experience.

Figure 4:
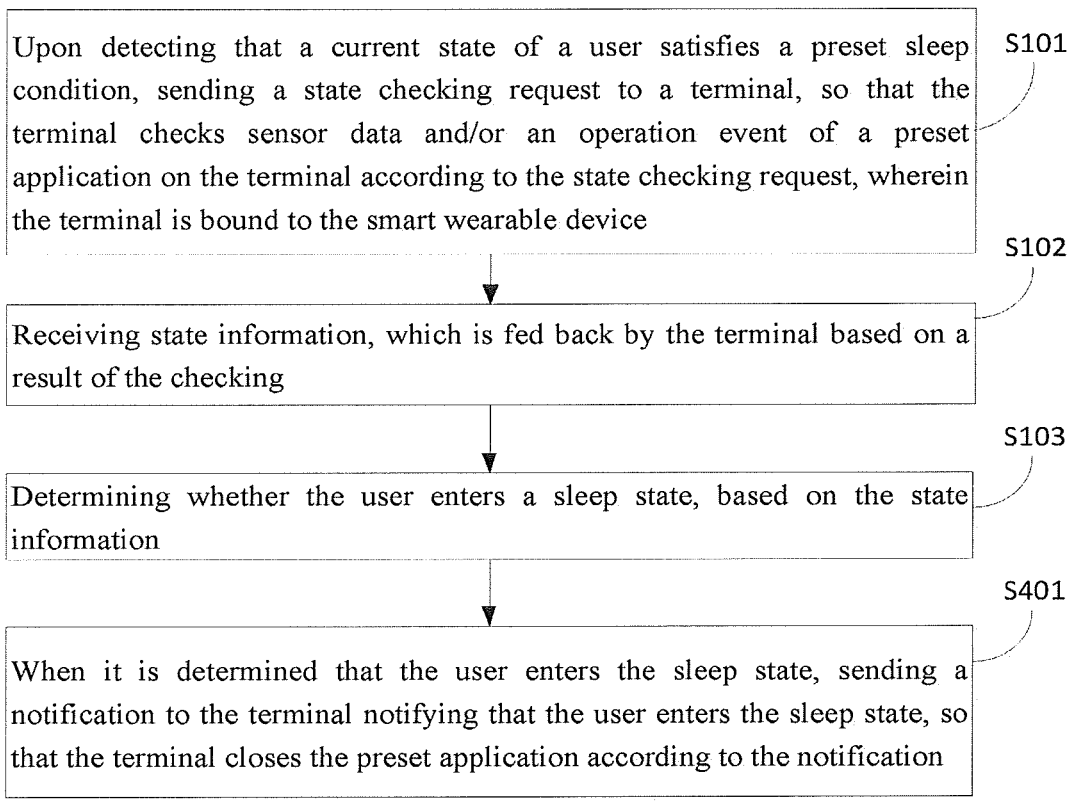
FIG. 4 is a flow chart showing a sleep state detection method according to still another exemplary embodiment.

As shown in FIG. 4, in an embodiment, the method further comprises step S401.

In step S401, when it is determined that the user enters the sleep state, a notification that the user enters the sleep state is sent to the terminal, so that the terminal closes the preset application according to the notification.

In this embodiment, after determining that the user enters the sleep state, the smart wearable device may send the notification that the user enters the sleep state, so that the terminal may close the predetermined application according to the notification, thereby reducing the power consumption of the terminal.

Figure 5:
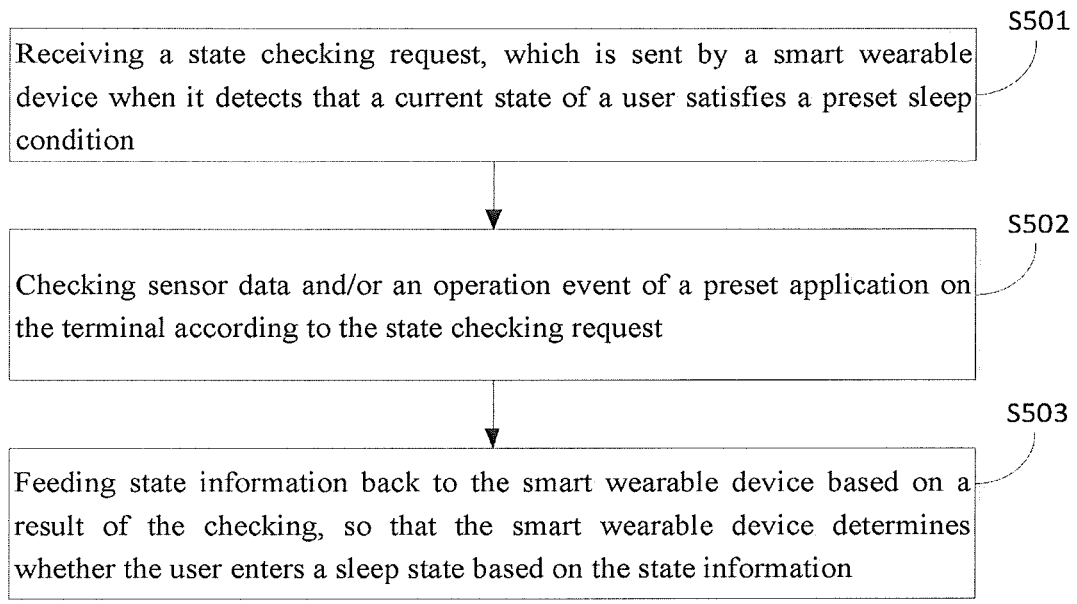
FIG. 5 is a flow chart showing a sleep state detection method according to an exemplary embodiment.

The disclosure also provides a sleep state detection method, which is applicable to a terminal device. As shown in FIG. 5, the method comprises steps S501-S503.

In step S501, a state checking request, which is sent by a smart wearable device when the smart wearable device detects that current status of a user satisfies a preset sleep condition, is received.

In step S502, sensor data and/or an operation event of a predetermined application on the terminal are checked, e.g., queried or accessed, according to the state checking request.

In step S503, state information based on the sensor data and/or the operation event of the predetermined application, is sent to the smart wearable device. In some examples, the smart wearable device may determine whether the user enters a sleep state based on the state information.

In this embodiment, when detecting that the current status of the user satisfies the preset sleep condition (i.e., when detecting that the user may have entered the sleep state), the smart wearable device sends a state checking request to the terminal, so that the terminal checks the sensor data and/or the operation event of the predetermined application on the terminal. The smart wearable device determines whether the user enters the sleep state based on the state information fed back by the terminal. In this manner, the smart wearable device determines whether the user enters the sleep state with the assistance of the terminal, thereby preventing the smart wearable device from miscalculating the user's sleep duration and even misjudging that a sleep quality problem occurs, ensuring the accuracy of calculating the user's sleep duration and improving the user experience.

The terminal may send the sensor data and/or the operation event of the predetermined application it acquires to the smart wearable device as the state information. Of course, it is also possible that the terminal determines the state information thereof (such as a current state indicating whether the predetermined application is in an awake state or a non-awake state) based on the sensor data and/or the operation event of the predetermined application and then sends the determined state information to the smart wearable device.

Determining whether the user enters the sleep state based on the sensor data on the terminal comprises: determining whether the terminal remains stationary for a preset time period. If so, it may be deemed that the user is asleep and it is thus determined that the user enters the sleep state. Otherwise, if the terminal is in a non-stationary state for the preset time period, it indicates that the terminal is still used by the user and it is thus determined that the user does not enter the sleep state.

Figure 6:
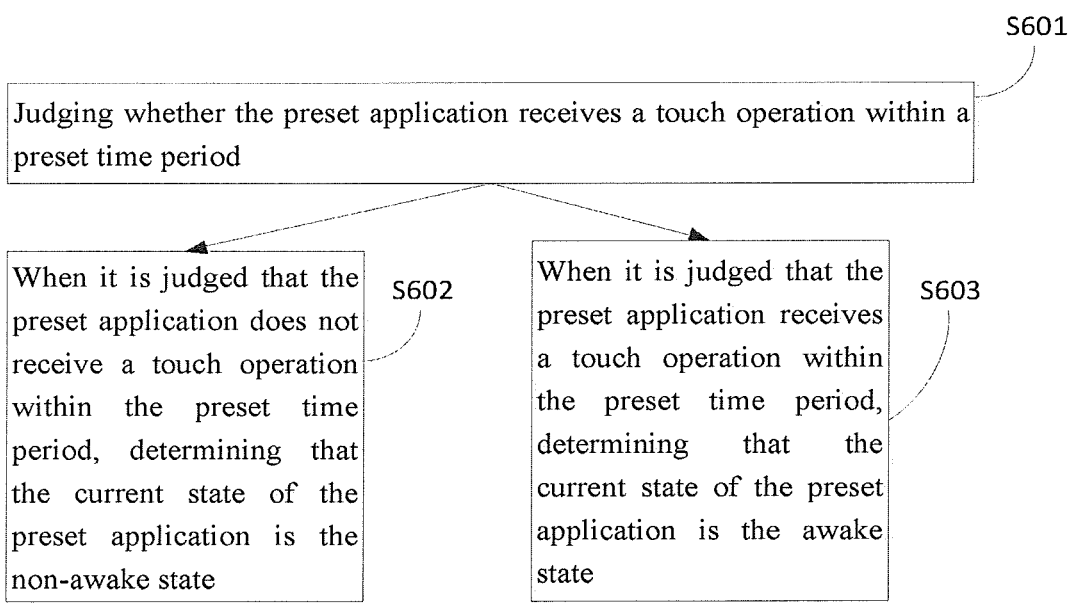
FIG. 6 is a flow chart showing step 502 in a sleep state detection method according to an exemplary embodiment.

As shown in FIG. 6, in an embodiment, a current state of the predetermined application comprises an awake state or a non-awake state, and the above-descried step S502 comprises steps S601-S603.

In step S601, it is determined whether the predetermined application receives a touch operation within a preset time period.

In step S602, when it is determined that the predetermined application does not receive a touch operation within the preset time period, it is determined that the current state of the predetermined application is the non-awake state.

In step S603, when it is determined that the predetermined application receives a touch operation within the preset time period, it is determined that the current state of the predetermined application is the awake state.

In this embodiment, if the predetermined application of the terminal does not receive a touch operation within the preset time period, it indicates that the terminal may not be used by the user. Then, it may be determined that the predetermined application is in the non-awake state. Otherwise, it is determined that the predetermined application is in the awake state.

Figure 7:
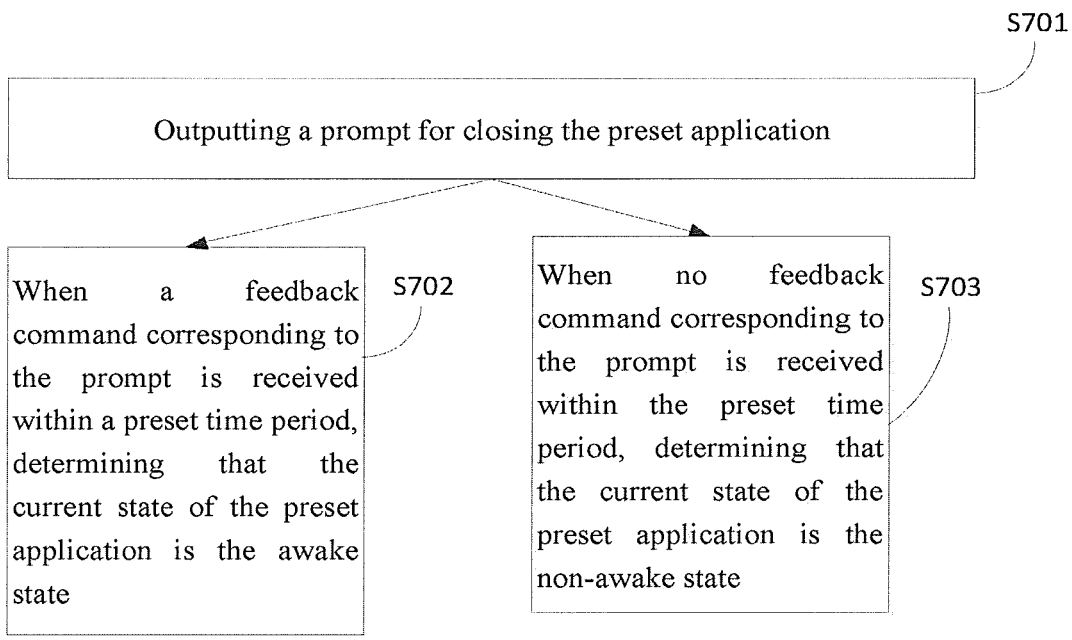
FIG. 7 is a flow chart showing step 502 in a sleep state detection method according to another exemplary embodiment.

As shown in FIG. 7, in an embodiment, a current state of the predetermined application comprises an awake state or a non-awake state, and the above-described step S502 may comprise steps S701-S703.

In step S701, a prompt for closing the predetermined application is output.

In step S702, when a feedback command corresponding to the prompt is received within a preset time period, it is determined that the current state of the predetermined application is the awake state.

In step S703, when no feedback command corresponding to the prompt is received within the preset time period, it is determined that the current state of the predetermined application is the non-awake state.

In this embodiment, the prompt for closing the predetermined application may be output. If the user does not enter the sleep state, he/she will choose whether to close the application. Accordingly, as long as a feedback command corresponding to the prompt is received within the preset time period, it indicates that the user is not asleep, i.e., the predetermined application is in the awake state. Otherwise, it is determined that the predetermined application is in the non-awake state.

Figure 8:
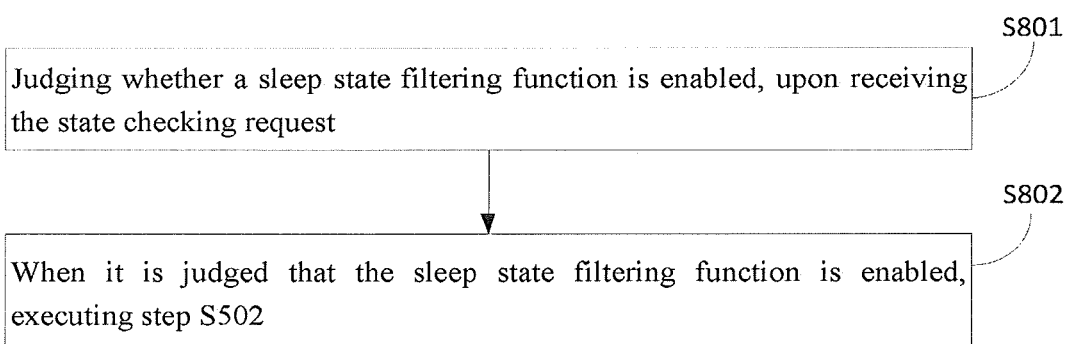
FIG. 8 is a flow chart showing a sleep state detection method according to another exemplary embodiment.

As shown in FIG. 8, in an embodiment, prior to checking the sensor data and/or the operation event of the predetermined application on the terminal, the method further comprises steps S801-S802.

In step S801, it is determined whether a sleep state filtering function is enabled, upon receiving the state checking request.

In step S802, when it is determined that the sleep state filtering function is enabled, the above-described step S502 is executed.

In this embodiment, the user may choose whether to enable the sleep state filtering function according to personal needs. If the function is enabled, then the state checking request is sent to the terminal when the smart wearable device detects that the current status of the user satisfies the preset sleep condition. The terminal checks the sensor data and/or the operation event of the predetermined application on the terminal according to the request. Accordingly, the smart wearable device determines the sleep state of the user based on the state information fed back by the terminal, so as to ensure the accuracy of the determination result. If the function is not enabled, then it is directly determined that the user enters the sleep state. In this manner, different needs of different users can be satisfied, thereby further improving the user experience.

Figure 9:
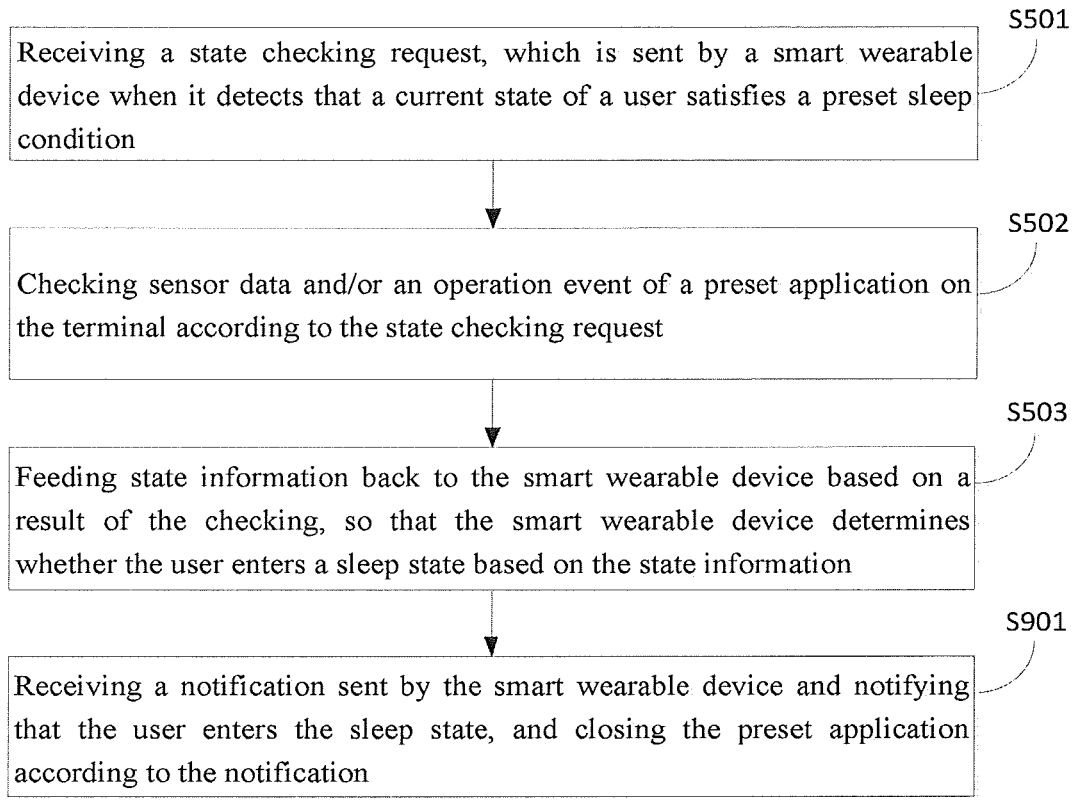
FIG. 9 is a flow chart showing a sleep state detection method according to yet another exemplary embodiment.

As shown in FIG. 9, in an embodiment, the method further comprises step S901.

In step S901, a notification sent by the smart wearable device and notifying that the user enters the sleep state is received, and the predetermined application is closed according to the notification.

In this embodiment, after determining that the user enters the sleep state, the smart wearable device may send the notification that the user enters the sleep state, so that the terminal may close the predetermined application according to the notification, thereby reducing the power consumption of the terminal.

Figure 10:
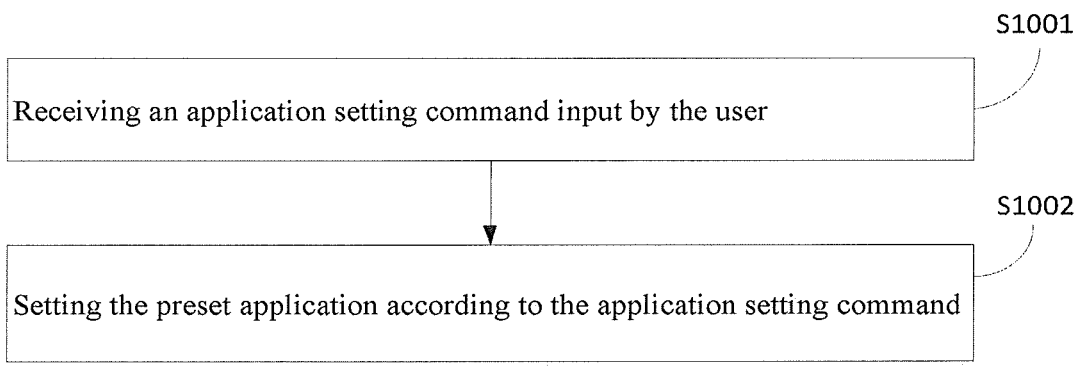
FIG. 10 is a flow chart showing a sleep state detection method according to still another exemplary embodiment.

As shown in FIG. 10, in an embodiment, the method further comprises steps S1001 and S1002.

In step S1001, an application setting command input by the user is received.

In step S1002, the predetermined application is set according to the application setting command.

In this embodiment, the user may set the predetermined application according to personal needs. For example, an application that is often used by the user before sleeping is set as the predetermined application, thereby ensuring the accuracy of calculating the user's sleep duration and improving the user experience.

In the following, apparatus embodiments of the disclosure which may be used to perform the method embodiments will be described.

Figure 11:
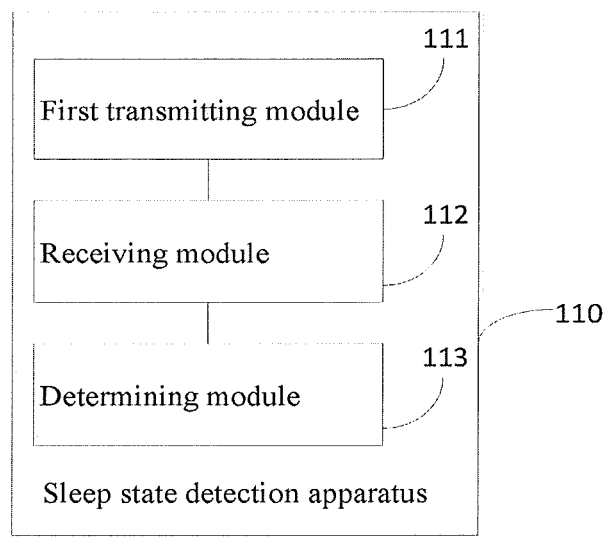
FIG. 11 is a block diagram showing a sleep state detection apparatus according to an exemplary embodiment.

FIG. 11 is a block diagram illustrating a sleep state detection apparatus according to an exemplary embodiment of the disclosure. The apparatus may be implemented by software, hardware or a combination thereof as a smart wearable device or a part of it. As shown in FIG. 11, the sleep state detection apparatus 110 comprises a first transmitting module 111, a receiving module 112, and a determining module 113.

The first transmitting module 111 is configured to, when it is detected that current status of a user satisfies a preset sleep condition, send a state checking request to a terminal. The terminal checks sensor data and/or an operation event of a preset application on the terminal according to the state checking request. In some examples, the terminal is associated with the smart wearable device.

The receiving module 112 is configured to receive state information, which is fed back by the terminal based on a result of the checking.

The determining module 113 is configured to determine whether the user enters a sleep state based on the state information received by the receiving module 112.

In this embodiment, when detecting that the current status of the user satisfies the preset sleep condition (i.e., when detecting that the user may have entered the sleep state), the smart wearable device sends the state checking request to the terminal. The terminal checks the sensor data and/or the operation event of the preset application on the terminal and the smart wearable device determines whether the user enters the sleep state based on the state information fed back by the terminal. In this manner, the smart wearable device determines whether the user enters the sleep state with the assistance of the terminal, thereby preventing the smart wearable device from miscalculating the user's sleep duration and even misjudging that a sleep quality problem occurs, ensuring the accuracy of calculating the user's sleep duration and improving the user experience.

The terminal may send the sensor data and/or the operation event of the predetermined application it acquires to the smart wearable device as the state information. Of course, it is also possible that the terminal determines the state information thereof (such a current state indicating whether the predetermined application is in as an awake state or a non-awake state) based on the sensor data and/or the operation event of the predetermined application and then sends the determined state information to the smart wearable device.

Determining whether the user enters the sleep state based on the sensor data on the terminal comprises: determining whether the terminal remains stationary for a preset time period. If so, it may be deemed that the user is asleep and it is thus determined that the user enters the sleep state. Otherwise, if the terminal is in a non-stationary state for the preset time period, it indicates that the terminal is still used by the user and it is thus determined that the user does not enter the sleep state.

Figure 12:
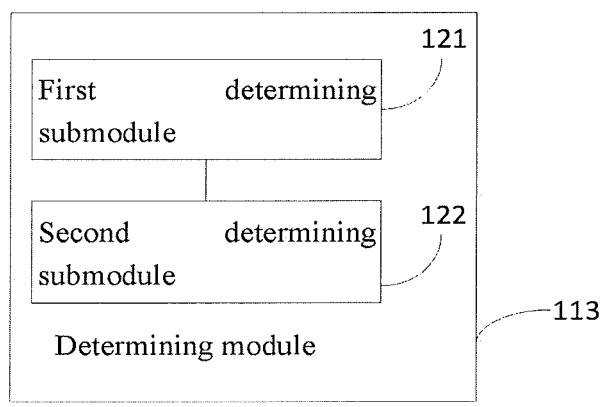
FIG. 12 is a block diagram showing a determining module in a sleep state detection apparatus according to an exemplary embodiment.

As shown in FIG. 12, in an embodiment, a current state of the predetermined application comprises an awake state or a non-awake state, and the determining module 113 comprises a first determining submodule 121 and a second determining submobule 122.

The first determining submodule 121 is configured to determine that the user does not enter the sleep state, when the current state of the predetermined application is the awake state.

The second determining submobule 122 is configured to determine that the user enters the sleep state, when the current state of the predetermined application is the non-awake state.

In this embodiment, if it is detected that the user performs an operation with respect to the preset application, it is deemed that the predetermined application is in the awake state; otherwise, it is deemed that the predetermined application is in the non-awake state. In this manner, it is determined whether the user is in the sleep state based on whether the user operates the predetermined application (i.e., whether the predetermined application is in an awake state or in a sleep state). This can ensure the accuracy of the judgment, thereby improving the user experience.

Figure 13:
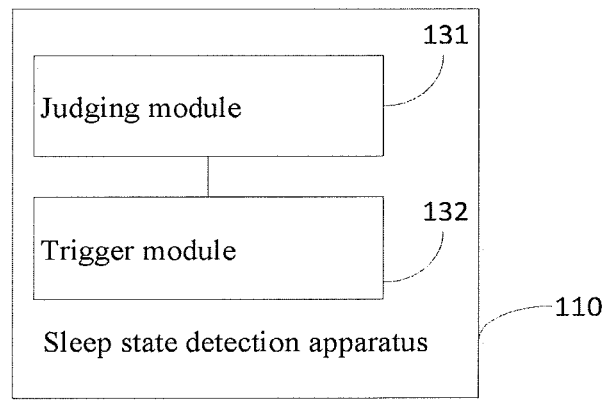
FIG. 13 is a block diagram showing another sleep state detection apparatus according to an exemplary embodiment.

As shown in FIG. 13, in an embodiment, the apparatus further comprises a judging module 131 and a trigging module 132.

The judging module 131 is configured to, when it is detected that the current state of the user satisfies the preset sleep condition, determine whether a sleep state filtering function is enabled.

The trigging module 132 is configured to, when it is determined that the sleep state filtering function is enabled, trigger the first transmitting module to send the state checking request to the terminal.

In this embodiment, the user may enable the sleep state filtering function according to personal needs. If the function is enabled, then the state checking request is sent to the terminal when the smart wearable device detects that the current status of the user satisfies the preset sleep condition. Accordingly, the sleep state of the user is determined based on the state information fed back by the terminal, so as to ensure the accuracy of the determination result. If the function is not enabled, then it is directly determined that the user enters the sleep state. In this manner, different needs of different users can be satisfied, thereby further improving the user experience.

Figure 14:
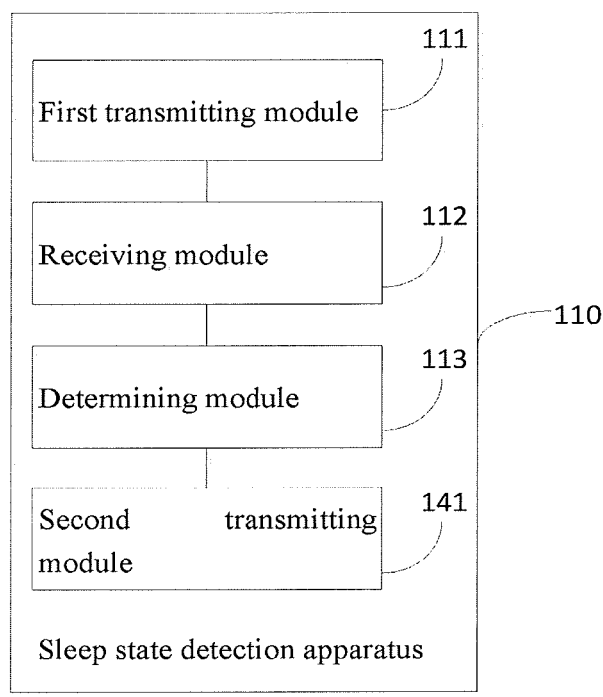
FIG. 14 is a block diagram showing yet another sleep state detection apparatus according to an exemplary embodiment.

As shown in FIG. 14, in an embodiment, the apparatus further comprises a second transmitting module 141. The second transmitting module 141 is configured to, when it is determined that the user enters the sleep state, send a notification to the terminal notifying that the user enters the sleep state. As such, the terminal may close the predetermined application according to the notification.

In this embodiment, after determining that the user enters the sleep state, the smart wearable device may send the notification that the user enters the sleep state, so that the terminal may close the predetermined application according to the notification, thereby reducing the power consumption of the terminal.

Figure 15:
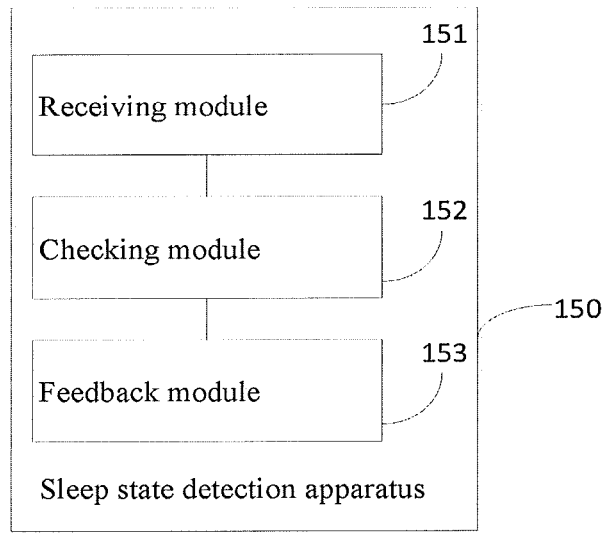
FIG. 15 is a block diagram showing a sleep state detection apparatus according to an exemplary embodiment.

FIG. 15 is a block diagram illustrating a sleep state detection apparatus according to an exemplary embodiment of the disclosure. The apparatus may be implemented by software, hardware or a combination thereof as a terminal or a part of it. As shown in FIG. 15, the sleep state detection apparatus 150 comprises a receiving module 151, a checking module 152, and a feedback module 153.

The receiving module 151 is configured to receive a state checking request, which is sent by a smart wearable device when it detects that current status of a user satisfies a preset sleep condition. The terminal is associated with the smart wearable device.

The checking module 152 is configured to check, e.g., query or access, sensor data and/or an operation event of a predetermined application on the terminal according to the state checking request.

The feedback module 153 is configured to send state information to the smart wearable device. The state information is provided based on a checking result of the checking module 152, such as the sensor data and/or the operation event of the predetermined application on the terminal. As such, the smart wearable device may determine whether the user enters a sleep state based on the state information.

In this embodiment, when detecting that the current status of the user satisfies the preset sleep condition (i.e., when detecting that the user may have entered the sleep state), the smart wearable device sends a state checking request to the terminal. The terminal checks the sensor data and/or the operation event of the predetermined application on the terminal, and the smart wearable device determines whether the user enters the sleep state based on the state information fed back by the terminal. In this manner, the smart wearable device determines whether the user enters the sleep state with the assistance of the terminal, thereby preventing the smart wearable device from miscalculating the user's sleep duration and even misjudging that a sleep quality problem occurs, ensuring the accuracy of calculating the user's sleep duration and improving the user experience.

The terminal may send the sensor data and/or the operation event of the predetermined application it acquires to the smart wearable device as the state information. Of course, it is also possible that the terminal determines the state information thereof (such as a current state indicating whether the predetermined application is in an awake state or a non-awake state) based on the sensor data and/or the operation event of the predetermined application and then sends the determined state information to the smart wearable device.

Determining whether the user enters the sleep state based on the sensor data on the terminal comprises: determining whether the terminal remains stationary for a preset time period. If so, it may be deemed that the user is asleep and it is thus determined that the user enters the sleep state. Otherwise, if the terminal is in a non-stationary state for the preset time period, it indicates that the terminal is still used by the user and it is thus determined that the user does not enter the sleep state.

Figure 16:
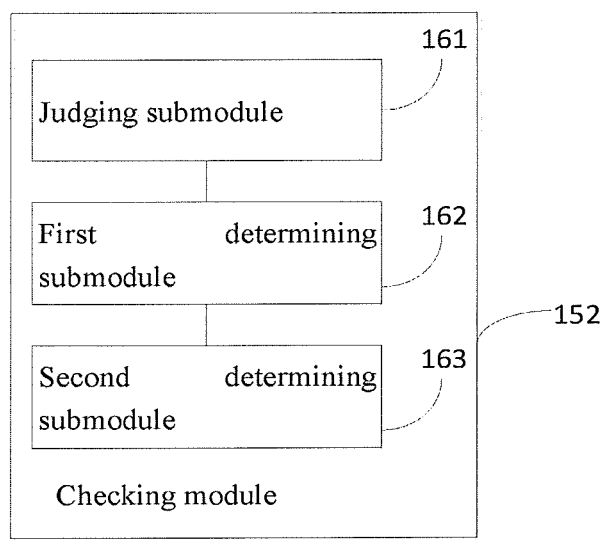
FIG. 16 is a block diagram showing a checking module in a sleep state detection apparatus according to an exemplary embodiment.

As shown in FIG. 16, in an embodiment, a current state of the predetermined application comprises an awake state or a non-awake state, and the checking module 152 comprises a judging submodule 161, a first determining submodule 162, and a second determining submodule 163.

The judging submodule 161 is configured to determine whether the predetermined application receives a touch operation within a preset time period.

The first determining submodule 162 is configured to, when the judging submodule 161 determines that the predetermined application does not receive a touch operation within the preset time period, determine that the current state of the predetermined application is the non-awake state.

The second determining submodule 163 is configured to, when the judging submodule 161 determines that the predetermined application receives a touch operation within the preset time period, determining that the current state of the predetermined application is the awake state.

In this embodiment, if the predetermined application of the terminal does not receive a touch operation within the preset time period, it indicates that the terminal may not be used by the user. Then, it may be determined that the predetermined application is in the non-awake state. Otherwise, it is determined that the predetermined application is in the awake state.

Figure 17:
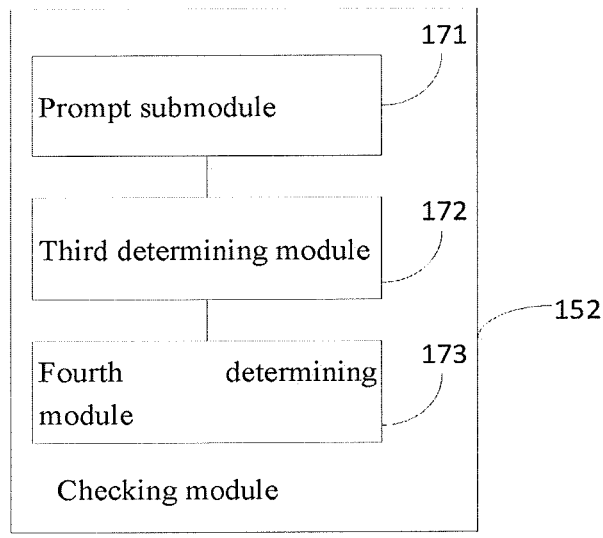
FIG. 17 is a block diagram showing another checking module in a sleep state detection apparatus according to an exemplary embodiment.

As shown in FIG. 17, in an embodiment, a current state of the predetermined application comprises an awake state or a non-awake state, and the checking module 152 comprises a prompt submodule 171, a third determining submodule 172, and a fourth determining submodule 173.

The prompt submodule 171 is configured to output a prompt for closing the predetermined application.

The third determining submodule 172 is configured to, when a feedback command corresponding to the prompt is received within a preset time period, determine that the current state of the predetermined application is the awake state.

The fourth determining submodule 173 is configured to, when no feedback command corresponding to the prompt is received within the preset time period, determine that the current state of the predetermined application is the non-awake state.

In this embodiment, the prompt for closing the predetermined application may be output. If the user does not enter the sleep state, he/she will choose whether to close the application. Accordingly, as long as a feedback command corresponding to the prompt is received within the preset time period, it indicates that the user is not asleep, i.e., the predetermined application is in the awake state. Otherwise, it is determined that the predetermined application is in the non-awake state.

Figure 18:
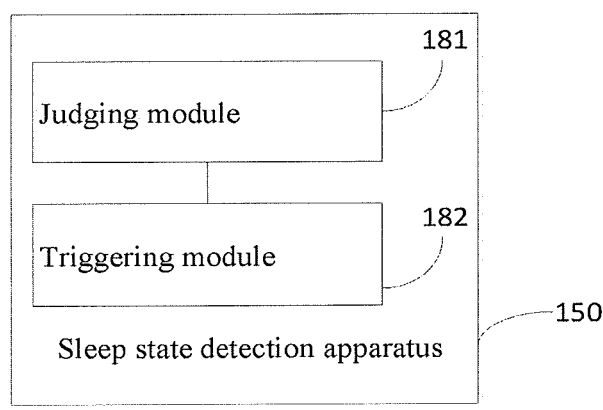
FIG. 18 is a block diagram showing another sleep state detection apparatus according to an exemplary embodiment.

As shown in FIG. 18, in an embodiment, the apparatus further comprises a judging module 181 and a trigger module 182.

The judging module 181 is configured to determine whether a sleep state filtering function is enabled, when the state checking request is received.

The trigger module 182 is configured to, when it is determined that the sleep state filtering function is enabled, trigger the checking module to check the sensor data and/or the operation event of the predetermined application on the terminal.

In this embodiment, the user may choose whether to enable the sleep state filtering function according to personal needs. If the function is enabled, then the state checking request is sent to the terminal when the smart wearable device detects that the current status of the user satisfies the preset sleep condition. The terminal checks the sensor data and/or the operation event of the predetermined application on the terminal according to the request. Accordingly, the smart wearable device determines the sleep state of the user based on the state information fed back by the terminal, so as to ensure the accuracy of the determination result. If the function is not enabled, then it is directly determined that the user enters the sleep state. In this manner, different needs of different users can be satisfied, thereby further improving the user experience.

Figure 19:
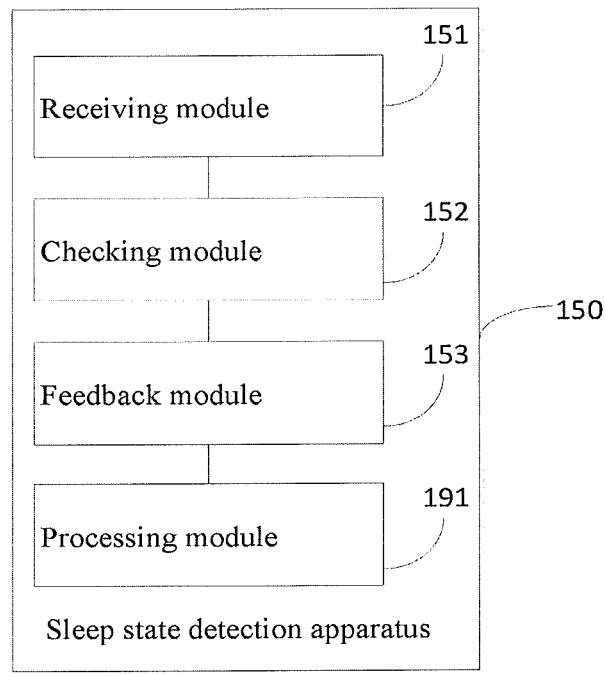
FIG. 19 is a block diagram showing yet another sleep state detection apparatus according to an exemplary embodiment.

As shown in FIG. 19, in an embodiment, the apparatus further comprises a processing module 191 configured to receive a notification sent by the smart wearable device and notifying that the user enters the sleep state. In some examples, the processing module 191 is configured to close the predetermined application according to the notification.

In this embodiment, after determining that the user enters the sleep state, the smart wearable device may send the notification that the user enters the sleep state. As such, the terminal may close the predetermined application according to the notification, thereby reducing the power consumption of the terminal.

Figure 20:
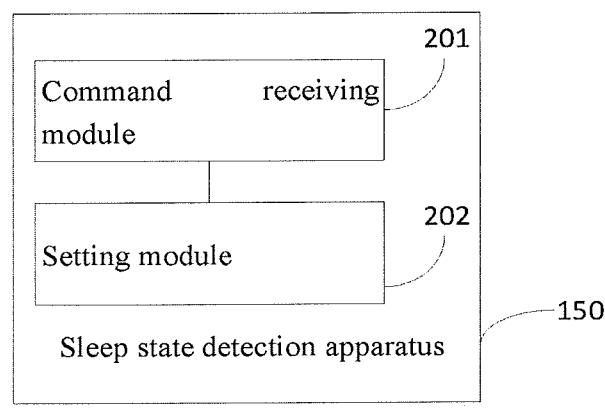
FIG. 20 is a block diagram showing still another sleep state detection apparatus according to an exemplary embodiment.

As shown in FIG. 20, in an embodiment, the apparatus further comprises a command receiving module 201 and a setting module 202.

The command receiving module 201 is configured to receive an application setting command input by the user.

The setting module 202 is configured to set the predetermined application according to the application setting command.

In this embodiment, the user may set the preset application according to personal needs. For example, an application that is often used by the user before sleeping is set as the predetermined application, thereby ensuring the accuracy of calculating the user's sleep duration and improving the user experience.

In accordance with some embodiments of the disclosure, a sleep state detection system includes a terminal and a smart wearable device.

The smart wearable device is configured to: upon detecting that current status of a user satisfies a preset sleep condition, send a state checking request to the terminal, so that the terminal checks sensor data and/or an operation event of a predetermined application on the terminal according to the state checking request, wherein the terminal is associated with the smart wearable device; receive state information, which is fed back by the terminal based on a result of the checking; and determine whether the user enters a sleep state based on the state information.

The terminal is configured to: receive the state checking request, which is sent by the smart wearable device when it detects that the current status of the user satisfies the preset sleep condition; check the sensor data and/or the operation event of the predetermined application on the terminal according to the state checking request; and feed the state information back to the smart wearable device based on the result of the checking, so that the smart wearable device determines whether the user enters the sleep state based on the state information.

In accordance with some embodiments of the disclosure, a sleep state detection apparatus includes a processor and a memory for storing instructions executable by the processor.

The processor is configured to: upon detecting that current status of a user satisfies a preset sleep condition, send a state checking request to a terminal, so that the terminal checks sensor data and/or an operation event of a predetermined application on the terminal according to the state checking request, wherein the terminal is associated with a smart wearable device; receive state information, which is fed back by the terminal based on a result of the checking; and determine whether the user enters a sleep state, based on the state information.

The processor may be further configured such that the state information comprises a current state indicating whether the predetermined application is in an awake state or a non-awake state. Also, the determining whether the user enters the sleep state based on the state information comprises: determining that the user does not enter the sleep state, when the current state of the predetermined application is the awake state; and determining that the user enters the sleep state, when the current state of the predetermined application is the non-awake state.

The processor may be further configured to:
upon detecting that the current status of the user satisfies the preset sleep condition, determine whether a sleep state filtering function is enabled,
wherein when it is determined that the sleep state filtering function is enabled, the state checking request is sent to the terminal.

The processor may be further configured to:
when it is determined that the user enters the sleep state, send a notification to the terminal notifying that the user enters the sleep state, so that the terminal may close the preset application according to the notification.

In accordance with some embodiments of the disclosure, a sleep state detection apparatus includes a processor and a memory for storing instructions executable by the processor.

The processor is configured to: receive a state checking request, which is sent by a smart wearable device when the smart wearable device detects that current status of a user satisfies a preset sleep condition; check sensor data and/or an operation event of a predetermined application on a terminal according to the state checking request; send state information to the smart wearable device based on a result of the checking, so that the smart wearable device may determine whether the user enters a sleep state based on the state information.

The processor may be further configured such that:
a current state of the predetermined application comprises an awake state or a non-awake state, and the checking the sensor data and/or the operation event of the predetermined application on the terminal comprises:
determining whether the predetermined application receives a touch operation within a preset time period;
when it is determined that the predetermined application does not receive a touch operation within the preset time period, determining that the current state of the predetermined application is the non-awake state; and
when it is determined that the predetermined application receives a touch operation within the preset time period, determining that the current state of the predetermined application is the awake state.

The processor may be further configured such that:
a current state of the predetermined application comprises an awake state or a non-awake state, and the checking the sensor data and/or the operation event of the predetermined application on the terminal comprises:
outputting a prompt for closing the predetermined application;
when a feedback command corresponding to the prompt is received within a preset time period, determining that the current state of the predetermined application is the awake state; and
when no feedback command corresponding to the prompt is received within the preset time period, determining that the current state of the predetermined application is the non-awake state.

In an embodiment, the processor may be further configured to: prior to checking the sensor data and/or the operation event of the predetermined application on the terminal,
determine whether a sleep state filtering function is enabled, upon receiving the state checking request, wherein
when it is determined that the sleep state filtering function is enabled, the sensor data and/or the operation event of the predetermined application on the terminal are checked.

The processor may be further configured to:
receive a notification sent by the smart wearable device and notifying that the user enters the sleep state; and
close the predetermined application according to the notification.

The processor may be further configured to:
receive an application setting command input by the user; and
set the preset application according to the application setting command.

It is noted that the various modules, submodules, units, or components described in the present disclosure can be implemented using any suitable technology. In an example, a module, submodule, unit, or component can be implemented using circuitry such as an integrated circuit (IC). In an example, a module, submodule, unit, or component can be implemented as processing circuitry executing software instructions.

Figure 21:
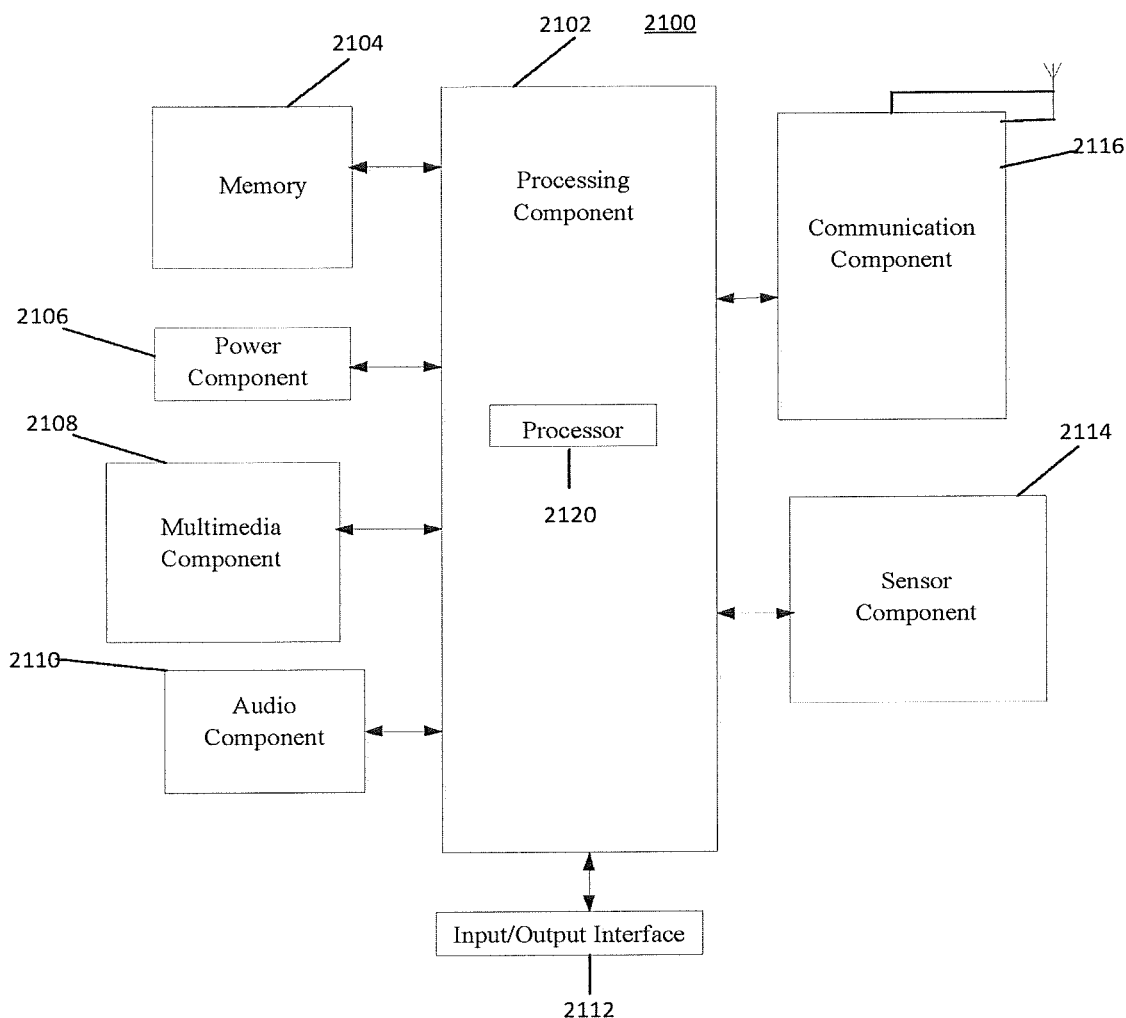
FIG. 21 is a block diagram of a sleep state detection apparatus according to an exemplary embodiment.

FIG. 21 is a block diagram of a sleep state detection apparatus 2100, which is applicable to a terminal device, according to an exemplary embodiment. For example, the apparatus 2100 may be a mobile phone, a computer, a digital broadcasting device, a messaging device, a game console, a tablet, a medical device, a fitness equipment, a personal digital assistant or the like.

Referring to FIG. 21, the apparatus 2100 may comprise one or more of the following components: a processing component 2102, a memory 2104, a power supply component 2106, a multimedia component 2108, an audio component 2110, an input/output (I/O) interface 2112, a sensor component 2114, and a communication component 2116.

The processing component 2102 typically controls overall operations of the apparatus 2100, such as the operations associated with display, telephone calls, data communications, camera operations, and recording operations. The processing component 2102 may include one or more processors 2120 to execute instructions to perform all or part of the steps in the above described methods. Moreover, the processing component 2102 may include one or more modules which facilitate the interaction between the processing component 2102 and other components. For instance, the processing component 2102 may include a multimedia module to facilitate the interaction between the multimedia component 2108 and the processing component 2102.

The memory 2104 is configured to store various types of data to support the operation of the apparatus 2100. Examples of such data include instructions for any applications or methods operated on the apparatus 2100, contact data, phonebook data, messages, pictures, video, etc. The memory 2104 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 2106 provides power to various components of the apparatus 2100. The power component 2106 may include a power supply management system, one or more power sources, and any other components associated with the generation, management, and distribution of power in the apparatus 2100.

The multimedia component 2108 includes a screen providing an output interface between the apparatus 2100 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 2108 includes a front camera and/or a rear camera. The front camera and/or the rear camera may receive an external multimedia datum while the apparatus 2100 is in an operation mode, such as a photographing mode or a video mode. Each of the front camera and the rear camera may be a fixed optical lens system or have focus and optical zoom capability.

The audio component 2110 is configured to output and/or input audio signals. For example, the audio component 2110 includes a microphone (MIC) configured to receive an external audio signal when the apparatus 2100 is in an operation mode, such as a call mode, a recording mode, and a voice recognition mode. The received audio signal may be further stored in the memory 2104 or transmitted via the communication component 2116. In some embodiments, the audio component 2110 further includes a speaker to output audio signals.

The I/O interface 2112 provides an interface between the processing component 2102 and peripheral interface modules, such as a keyboard, a click wheel, buttons, and the like. The buttons may include, but are not limited to, a home button, a volume button, a starting button, and a locking button.

The sensor component 2114 includes one or more sensors to provide status assessments of various aspects of the apparatus 2100. For instance, the sensor component 2114 may detect an open/closed status of the apparatus 2100, relative positioning of components, e.g., the display and the keypad, of the apparatus 2100, a change in position of the apparatus 2100 or a component of the apparatus 2100, a presence or absence of user contact with the apparatus 2100, an orientation or an acceleration/deceleration of the apparatus 2100, and a change in temperature of the apparatus 2100. The sensor component 2114 may include a proximity sensor configured to detect the presence of nearby objects without any physical contact. The sensor component 2114 may also include a light sensor, such as a CMOS or CCD image sensor, for use in imaging applications. In some embodiments, the sensor component 2114 may also include an accelerometer sensor, a gyroscope sensor, a magnetic sensor, a pressure sensor, or a temperature sensor.

The communication component 2116 is configured to facilitate communication, wired or wirelessly, between the apparatus 2100 and other devices. The apparatus 2100 can access a wireless network based on a communication standard, such as WiFi, 2G, or 3G, or a combination thereof. In one exemplary embodiment, the communication component 2116 receives a broadcast signal or broadcast associated information from an external broadcast management system via a broadcast channel. In one exemplary embodiment, the communication component 2116 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the apparatus 2100 may be implemented with one or more application specific integrated circuits (ASICs), digital signal processors (DSPs), digital signal processing devices (DSPDs), programmable logic devices (PLDs), field programmable gate arrays (FP-GAs), controllers, micro-controllers, microprocessors, or other electronic components, for performing the above described methods.

The exemplary embodiments also provides a non-transitory computer-readable storage medium containing instructions, such as the memory 2104 containing instructions which may be executed by the processing component 2120 of the apparatus 2100 to perform the above methods. For example, the non-volatile computer-readable storage medium may be a ROM, a RAM, a CD-ROM, a tape, a floppy disc, an optical data storage device or the like.

Figure 22:
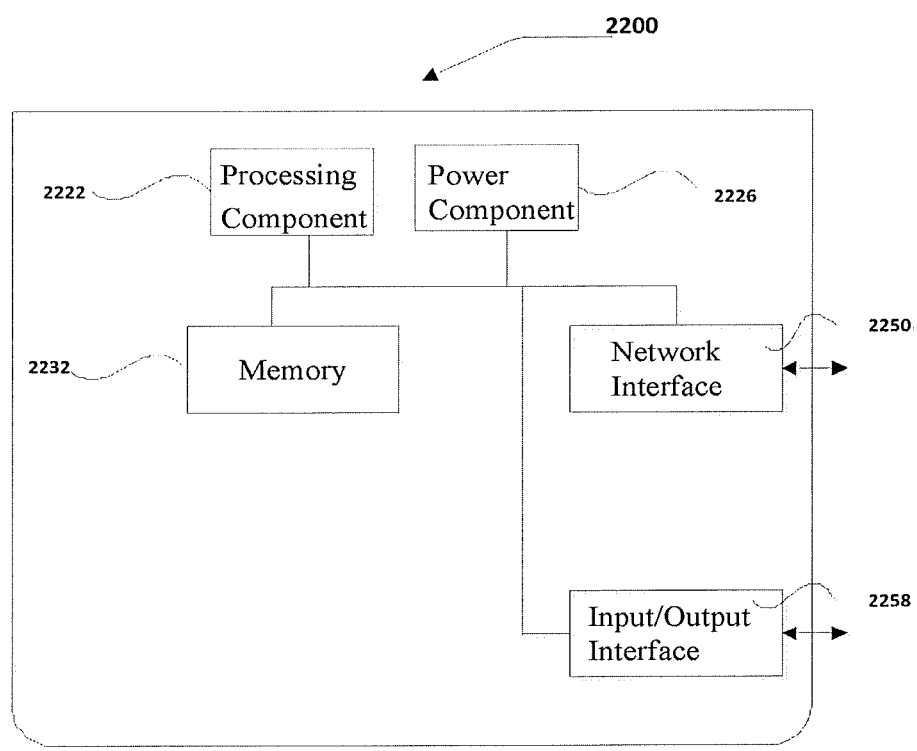
FIG. 22 is a block diagram of another sleep state detection apparatus according to an exemplary embodiment.

FIG. 22 is a block diagram illustrating a sleep state detection apparatus 2200 according to an exemplary embodiment. For example, the apparatus 2200 may be provided as a server or a smart wearable device. As shown in FIG. 22, the apparatus 2200 comprises: a processing component 2222 which further comprises one or more processors; and memory resources represented by a memory 2232 for storing instructions executable by the processing component 2222, such as applications. The applications stored in the memory 2232 may comprise one or more modules, each module corresponding to a group of instructions. In addition, the processing component 2222 is configured to execute instructions to perform the above payment verification method.

The apparatus 2200 may further comprise a power component 2226 configured to perform power management for the apparatus 2200, a wired or wireless network interface 2250 configured to connect the apparatus 2200 to a network, and an input/output I/O interface 2258. The apparatus 2200 may operate an operating system stored in the memory 2232, such as Windows Server™, Mac OS X™, Unix™, Linux™, FreeBSD™ or the like.

In accordance with some embodiments, a non-transitory computer-readable storage medium contains instructions, which when executed by the processor of the apparatus 2100 cause the apparatus 2100 to perform the above-described sleep state detection method. The method comprises:
receiving a state checking request, which is sent by a smart wearable device when the smart wearable device detects that current status of a user satisfies a preset sleep condition;
checking sensor data and/or an operation event of a predetermined application on the terminal according to the state checking request; and
sending state information to the smart wearable device based on a result of the checking, so that the smart wearable device may determine whether the user enters a sleep state based on the state information.

In an embodiment, a current state of the predetermined application comprises an awake state or a non-awake state, and the checking the sensor data and/or the operation event of the predetermined application on the terminal comprises:
determining whether the predetermined application receives a touch operation within a preset time period;
when it is determined that the predetermined application does not receive a touch operation within the preset time period, determining that the current state of the predetermined application is the non-awake state; and
when it is determined that the predetermined application receives a touch operation within the preset time period, determining that the current state of the predetermined application is the awake state.

In an embodiment, a current state of the predetermined application comprises an awake state or a non-awake state, and the checking the sensor data and/or the operation event of the predetermined application on the terminal comprises:
outputting a prompt for closing the predetermined application;
when a feedback command corresponding to the prompt is received within a preset time period, determining that the current state of the predetermined application is the awake state; and
when no feedback command corresponding to the prompt is received within the preset time period, determining that the current state of the predetermined application is the non-awake state.

In an embodiment, the method further comprises: prior to checking the sensor data and/or the operation event of the predetermined application on the terminal,
determining whether a sleep state filtering function is enabled, upon receiving the state checking request, wherein when it is determined that the sleep state filtering function is enabled, the sensor data and/or the operation event of the predetermined application on the terminal are checked.

In an embodiment, the method further comprises:

receiving a notification sent by the smart wearable device and notifying that the user enters the sleep state, and closing the predetermined application according to the notification.

In an embodiment, the method further comprises:

receiving an application setting command input by the user; and setting the predetermined application according to the application setting command.

In accordance with some embodiments, a non-transitory computer-readable storage medium contains instructions, which when executed by the processor of the apparatus 2200 cause the apparatus 2200 to perform the above-described sleep state detection method. The method comprises:

upon detecting that current status of a user satisfies a preset sleep condition, sending a state checking request to a terminal, so that the terminal checks sensor data and/or an operation event of a predetermined application on the terminal according to the state checking request, wherein the terminal is associated with the smart wearable device;

receiving state information, which is sent by the terminal based on a result of the checking; and determining whether the user enters a sleep state, based on the state information.

In an embodiment, a current state of the predetermined application comprises an awake state or a non-awake state, and the determining whether the user enters the sleep state based on the state information comprises:

determining that the user does not enter the sleep state, when the current state of the predetermined application is the awake state; and determining that the user enters the sleep state, when the current state of the predetermined application is the non-awake state.

In an embodiment, the method further comprises:

upon detecting that the current status of the user satisfies the preset sleep condition, determining whether a sleep state filtering function is enabled, wherein when it is determined that the sleep state filtering function is enabled, the state checking request is sent to the terminal.

In an embodiment, the method further comprises:

when it is determined that the user enters the sleep state, sending a notification to the terminal notifying that the user enters the sleep state, so that the terminal may close the predetermined application according to the notification.

Other embodiments of the disclosure will be apparent to those skilled in the art from consideration of the specification and practice of the embodiments disclosed here. This application is intended to cover any variations, uses, or adaptations of the disclosure following the general principles thereof and including such variations, uses, or adaptations that are not explicitly described in the present disclosure as come within known or customary practice in the art. It is intended that the specification and examples be considered as exemplary only.

It will be appreciated that the present disclosure is not limited to the exact construction that has been described above and illustrated in the accompanying drawings, and that various modifications and changes can be made without departing from the scope thereof.

The invention claimed is:

1. A sleep state detection method, comprising:

upon detecting that current status of a user satisfies a preset sleep condition, determining, by a smart wearable device, whether a sleep state filtering function is enabled in the smart wearable device; and upon detecting that the current status of the user satisfies the preset sleep condition and when the sleep state filtering function is determined to be enabled, sending, by the smart wearable device, a state checking request to a terminal associated with the smart wearable device, the state checking request instructing the terminal to provide state information based on sensor data or an operation event of a predetermined application on the terminal, receiving the state information from the terminal, and determining whether the user enters a sleep state based on the state information.

2. The method according to claim 1, wherein the state information comprises a current state of the predetermined application indicating whether the predetermined application is in an awake state or a non-awake state, and the determining whether the user enters the sleep state based on the state information comprises:

determining that the user does not enter the sleep state, when the current state of the predetermined application is the awake state; and determining that the user enters the sleep state, when the current state of the predetermined application is the non-awake state.

3. The method according to claim 1, further comprising:

when it is determined that the user enters the sleep state, sending a notification to the terminal notifying that the user enters the sleep state.

4. A sleep state detection method, comprising:

receiving, by a terminal, a state checking request from a smart wearable device indicating that the smart wearable device detects that current status of a user satisfies a preset sleep condition;

determining, by the terminal, whether a sleep state filtering function is enabled in the smart wearable device upon receiving the state checking request; and when it is determined that the sleep state filtering function is enabled, checking, by the terminal, sensor data or an operation event of a predetermined application on the terminal according to the state checking request, and sending state information to the smart wearable device based on the sensor data or the operation event of the predetermined application on the terminal, so that the smart wearable device determines whether the user enters a sleep state based on the state information.

5. The method according to claim 4, wherein the state information comprises a current state of the predetermined application indicating whether the predetermined application is in an awake state or a non-awake state, and checking the sensor data or the operation event of the predetermined application on the terminal comprises:

determining whether the predetermined application receives a touch operation within a preset time period;

when it is determined that the predetermined application does not receive a touch operation within the preset time period, determining that the current state of the predetermined application is the non-awake state; and when it is determined that the predetermined application receives a touch operation within the preset time period, determining that the current state of the predetermined application is the awake state.

6. The method according to claim 4, wherein the state information comprises a current state of the predetermined application indicating whether the predetermined application is in an awake state or a non-awake state, and checking the sensor data or the operation event of the predetermined application on the terminal comprises:

outputting a prompt for closing the predetermined application;

when a feedback command corresponding to the prompt is received within a preset time period, determining that the current state of the predetermined application is the awake state; and when no feedback command corresponding to the prompt is received within the preset time period, determining that the current state of the predetermined application is the non-awake state.

7. The method according to claim 4, further comprising:
receiving a notification from the smart wearable device, the notification notifying that the user enters the sleep state; and
closing the predetermined application according to the notification.

8. The method according to claim 4, further comprising:
receiving an application setting command; and
setting the predetermined application according to the application setting command.

9. An apparatus, comprising:
a processor; and
a memory for storing instructions executable by the processor,
wherein the processor is configured to:
upon detecting that current status of a user satisfies a preset sleep condition, determine whether a sleep state filtering function is enabled in the apparatus; and
upon detecting that the current status of the user satisfies the preset sleep condition and when the sleep state filtering function is determined to be enabled,
send a state checking request to a terminal associated with the apparatus, the state checking request instructing the terminal to provide state information based on sensor data or an operation event of a predetermined application on the terminal,
receive the state information from the terminal, and determine whether the user enters a sleep state based on the state information.

10. The apparatus of claim 9, wherein the state information comprises a current state of the predetermined application indicating whether the predetermined application is in an awake state or a non-awake state, and the processor is further configured to:
determine that the user does not enter the sleep state, when the current state of the predetermined application is the awake state; and
determine that the user enters the sleep state, when the current state of the predetermined application is the non-awake state.

11. The apparatus of claim 9, wherein the processor is further configured to:
when it is determined that the user enters the sleep state, send a notification to the terminal notifying that the user enters the sleep state.

12. An apparatus, comprising:
a processor; and
a memory for storing instructions executable by the processor,
wherein the processor is configured to:
receive a state checking request from a smart wearable device indicating that the smart wearable device detects that current status of a user satisfies a preset sleep condition;
determine whether a sleep state filtering function is enabled in the smart wearable device upon receiving the state checking request; and
when it is determined that the sleep state filtering function is enabled,
check sensor data or an operation event of a predetermined application on the apparatus according to the state checking request; and
send state information to the smart wearable device based on the sensor data or the operation event of the predetermined application on the apparatus, so that the smart wearable device determines whether the user enters a sleep state based on the state information.

13. The apparatus of claim 12, wherein the state information comprises a current state of the predetermined application indicating whether the predetermined application is in an awake state or a non-awake state, and the processor is further configured to:
determine whether the predetermined application receives a touch operation within a preset time period;
when it is determined that the predetermined application does not receive a touch operation within the preset time period, determine that the current state of the predetermined application is the non-awake state; and
when it is determined that the predetermined application receives a touch operation within the preset time period, determine that the current state of the predetermined application is the awake state.

14. The apparatus of claim 12, wherein the state information comprises a current state of the predetermined application indicating whether the predetermined application is in an awake state or a non-awake state, and the processor is further configured to:
output a prompt for closing the predetermined application;
when a feedback command corresponding to the prompt is received within a preset time period, determine that the current state of the predetermined application is the awake state; and
when no feedback command corresponding to the prompt is received within the preset time period, determine that the current state of the predetermined application is the non-awake state.

15. The apparatus of claim 12, wherein the processor is further configured to:
receive a notification from the smart wearable device, the notification notifying that the user enters the sleep state; and
close the predetermined application according to the notification.

16. The apparatus of claim 12, wherein the processor is further configured to:
receive an application setting command; and
set the predetermined application according to the application setting command.

* * * * *